US009925186B2

(12) United States Patent
Cincotta

(10) Patent No.: US 9,925,186 B2
(45) Date of Patent: Mar. 27, 2018

(54) METHOD OF TREATING METABOLIC DISORDERS AND DEPRESSION WITH DOPAMINE RECEPTOR AGONISTS

(71) Applicant: VeroScience LLC, Tiverton, RI (US)

(72) Inventor: Anthony H. Cincotta, Tiverton, RI (US)

(73) Assignee: VeroScience LLC, Tiverton, RI (US)

( * ) Notice: Subject to any disclaimer, the term of this patent is extended or adjusted under 35 U.S.C. 154(b) by 0 days.

(21) Appl. No.: 14/814,018

(22) Filed: Jul. 30, 2015

(65) Prior Publication Data

US 2015/0335641 A1 Nov. 26, 2015

Related U.S. Application Data

(60) Division of application No. 13/774,739, filed on Feb. 22, 2013, now Pat. No. 9,205,084, which is a continuation of application No. 12/144,617, filed on Jun. 23, 2008, now abandoned.

(60) Provisional application No. 60/945,555, filed on Jun. 21, 2007.

(51) Int. Cl.

| | |
|---|---|
| ***A61K 31/55*** | (2006.01) |
| ***A61K 31/50*** | (2006.01) |
| ***A61K 31/517*** | (2006.01) |
| ***A61K 31/44*** | (2006.01) |
| ***A61K 31/135*** | (2006.01) |
| ***A61K 31/4985*** | (2006.01) |
| ***A61K 31/00*** | (2006.01) |
| ***A61K 45/06*** | (2006.01) |
| ***A61K 31/48*** | (2006.01) |

(52) U.S. Cl.

CPC .......... *A61K 31/4985* (2013.01); *A61K 31/00* (2013.01); *A61K 31/48* (2013.01); *A61K 45/06* (2013.01)

(58) Field of Classification Search

CPC ...................................................... A61K 31/48
USPC .. 514/213.01, 217.07, 250, 266.1, 288, 295, 514/649, 866
See application file for complete search history.

(56) References Cited

U.S. PATENT DOCUMENTS

| | | | |
|---|---|---|---|
| 4,659,715 | A | 4/1987 | Meier et al. |
| 4,783,469 | A | 11/1988 | Meier et al. |
| 4,791,125 | A | 12/1988 | Clark |
| 5,006,526 | A | 4/1991 | Meier et al. |
| 5,344,832 | A | 9/1994 | Cincotta et al. |
| 5,468,755 | A | 11/1995 | Cincotta et al. |
| 5,496,803 | A | 3/1996 | Meier et al. |
| 5,554,623 | A | 9/1996 | Cincotta et al. |
| 5,565,454 | A | 10/1996 | Cincotta |
| 5,585,347 | A | 12/1996 | Meier et al. |
| 5,626,860 | A | 5/1997 | Cincotta et al. |
| 5,635,512 | A | 6/1997 | Cincotta et al. |
| 5,654,313 | A | 8/1997 | Cincotta et al. |
| 5,668,155 | A | 9/1997 | Cincotta et al. |
| 5,679,685 | A | 10/1997 | Cincotta et al. |
| 5,688,794 | A | 11/1997 | Meier et al. |
| 5,696,128 | A | 12/1997 | Cincotta et al. |
| 5,700,795 | A | 12/1997 | Cincotta et al. |
| 5,700,800 | A | 12/1997 | Cincotta et al. |
| 5,712,265 | A | 1/1998 | Cincotta et al. |
| 5,714,519 | A | 2/1998 | Cincotta et al. |
| 5,716,932 | A | 2/1998 | Meier et al. |
| 5,716,933 | A | 2/1998 | Meier et al. |
| 5,716,957 | A | 2/1998 | Cincotta et al. |
| 5,716,962 | A | 2/1998 | Cincotta et al. |
| 5,719,160 | A | 2/1998 | Cincotta et al. |
| 5,731,287 | A | 3/1998 | Meier et al. |
| 5,731,312 | A | 3/1998 | Cincotta et al. |
| 5,741,503 | A | 4/1998 | Cincotta et al. |
| 5,744,477 | A | 4/1998 | Cincotta et al. |
| 5,750,519 | A | 5/1998 | Cincotta et al. |
| 5,756,513 | A | 5/1998 | Cincotta et al. |
| 5,760,047 | A | 6/1998 | Cincotta et al. |
| 5,792,748 | A | 8/1998 | Cincotta et al. |
| 5,830,895 | A | 11/1998 | Cincotta et al. |
| 5,854,255 | A | 12/1998 | Cincotta et al. |
| 5,866,584 | A | 2/1999 | Cincotta et al. |
| 5,872,127 | A | 2/1999 | Cincotta et al. |
| 5,872,133 | A | 2/1999 | Cincotta et al. |
| 5,877,183 | A | 3/1999 | Cincotta |
| 5,902,811 | A | 5/1999 | Cincotta |
| 5,905,083 | A | 5/1999 | Cincotta et al. |
| 6,004,972 | A | 12/1999 | Cincotta et al. |
| 6,071,914 | A | 6/2000 | Cincotta et al. |
| 6,075,020 | A | 6/2000 | Cincotta et al. |
| 6,855,707 | B2 | 2/2005 | Cincotta |
| 7,888,310 | B2 | 2/2011 | Cincotta |
| 8,021,681 | B2 | 9/2011 | Cincotta |

(Continued)

FOREIGN PATENT DOCUMENTS

| | | |
|---|---|---|
| CN | 1678313 | 10/2005 |
| RU | 2467743 | 11/2012 |

(Continued)

OTHER PUBLICATIONS

Wada et al., "Dose-dependent augmentation effect of bromocriptine in a case with refractory depression," *Prog Neuropsychopharmacol Biol Psychiatry*, 25(2):457-462, Feb. 2001.
Waehrens et al., "Bromocriptine and imipramine in endogenous depression. A double-blind controlled trial in out-patients," *J Affect Disord.*, 3(2):193-202, Jun. 1981.
Extended European Search Report in EP Application No. 08780943.0, dated Dec. 20, 2013, 7 pages.
Office Action in European Application No. 08780943.0, dated Nov. 9, 2015, 8 pages.
Restriction Requirement in U.S. Appl. No. 12/144,617, dated Jan. 20, 2011, 7 pages.
Non-final Office Action in U.S. Appl. No. 12/144,617, dated May 4, 2011, 9 pages.

(Continued)

*Primary Examiner* — Kevin E Weddington
(74) *Attorney, Agent, or Firm* — Fish & Richardson P.C.

(57) ABSTRACT

This invention relates to methods and formulations for treating metabolic disorders and depression. In some embodiments, the methods comprise administering a dopamine receptor agonist and an anti-depressant.

15 Claims, No Drawings

(56) References Cited

U.S. PATENT DOCUMENTS

| | | | |
|---|---|---|---|
| 8,137,992 | B2 | 3/2012 | Cincotta |
| 8,137,993 | B2 | 3/2012 | Cincotta |
| 8,137,994 | B2 | 3/2012 | Cincotta |
| 8,431,155 | B1 | 4/2013 | Cincotta et al. |
| 8,613,947 | B2 | 12/2013 | Cincotta et al. |
| 8,741,918 | B2 | 6/2014 | Cincotta |
| 8,821,915 | B2 | 9/2014 | Cincotta |
| 8,877,708 | B2 | 11/2014 | Cincotta |
| 9,192,576 | B2 | 11/2015 | Cincotta et al. |
| 9,205,084 | B2 | 12/2015 | Cincotta |
| 2001/0016582 | A1 | 8/2001 | Cincotta et al. |
| 2002/0187985 | A1 | 12/2002 | Cincotta |
| 2003/0087963 | A1 | 5/2003 | Senanayake et al. |
| 2004/0077679 | A1 | 4/2004 | Cincotta |
| 2004/0081678 | A1 | 4/2004 | Cincotta |
| 2004/0214887 | A1 | 10/2004 | Dasseux et al. |
| 2004/0220190 | A1 | 11/2004 | Cincotta |
| 2005/0054652 | A1 | 3/2005 | Cincotta |
| 2005/0054734 | A1 | 3/2005 | Cincotta |
| 2005/0215558 | A1 | 9/2005 | Cincotta |
| 2007/0015763 | A1 | 1/2007 | Romano |
| 2008/0200453 | A1 | 8/2008 | Cincotta |
| 2008/0293735 | A1 | 11/2008 | Cincotta |
| 2009/0137598 | A1 | 5/2009 | Cincotta |
| 2009/0143390 | A1 | 6/2009 | Cincotta |
| 2010/0035886 | A1 | 2/2010 | Cincotta et al. |
| 2013/0197005 | A1 | 8/2013 | Cincotta |
| 2013/0274246 | A1 | 10/2013 | Cincotta |
| 2014/0051685 | A1 | 2/2014 | Cincotta |
| 2014/0249136 | A1 | 9/2014 | Cincotta |
| 2014/0342975 | A1 | 11/2014 | Cincotta |
| 2015/0011554 | A1 | 1/2015 | Cincotta et al. |
| 2015/0024995 | A1 | 1/2015 | Cincotta |
| 2015/0335641 | A1 | 11/2015 | Cincotta |
| 2016/0038424 | A1 | 2/2016 | Cincotta et al. |

FOREIGN PATENT DOCUMENTS

| | | |
|---|---|---|
| WO | WO1993000092 | 1/1993 |
| WO | 1994/15211 | 7/1994 |
| WO | WO1995017170 | 6/1995 |
| WO | 1996/00396 | 1/1996 |
| WO | WO 2004/010946 | 2/2004 |
| WO | WO2004014362 | 2/2004 |

OTHER PUBLICATIONS

Final Office Action in U.S. Appl. No. 12/144,617, dated Dec. 6, 2011, 8 pages.

Restriction Requirement in U.S. Appl. No. 13/774,739, dated Dec. 10, 2013, 7 pages.

Non-final Office Action in U.S. Appl. No. 13/774,739, dated Mar. 20, 2014, 9 pages.

Final Office Action in U.S. Appl. No. 13/774,739, dated Oct. 21, 2014, 6 pages.

Ex Parte Quayle Office Action in U.S. Appl. No. 13/774,739, dated May 6, 2015, 5 pages.

Notice of Allowance in U.S. Appl. No. 13/774,739, dated Aug. 3, 2015, 5 pages.

International Search Report and Written Opinion for PCT/US2008/067953, dated Nov. 3, 2008, 5 pages.

International Preliminary Report on Patentability for PCT/US2008/067953, dated Dec. 22, 2009, 5 pages.

Office Action in Indian Application No. 240/KOLNP/2010, dated Mar. 20, 2015, 2 pages.

Mattox et al., "Dopamine Agonists for Reducing Depression Associated with Hyperprolactinemia", Journal of Reproductive Medicine, 31(8):694-698 (Aug. 1988).

Nordin et al., "Bromocriptine treatment of depressive disorders", Acta Psychiatrica Scandinavica, 64(1):25-33 (Jul. 1981).

Pip et al., "Modulation of Monoaminergic Neural Circuits Potential for the Treatment of Type 2 Diabetes Mellitus", Treat Endocrinol., 1(2)11-78 (2002).

Armentero et al., "Dopamine Receptor Agonists Media europrotection in malonate-Induced striatal lesion in the Rat," Experimental Neurology, Dec. 2002, 178(2):301-305.

Arteriosclerosis/atherosclerosis Definition-Diseases and Condition, by Mayo Clinic staff, May 2014, accessed on Oct. 8, 2014; available at http://www.mayoclinic.org/diseases-conditions/arteriosclerosis-atherosclerosis/basics/definition/con-20026972, 9 pages.

Breen et al., "Insulin increases reendothelialization and inhibits cell migration and neointimal growth after arterial injury," Arterioscler Thromb Vase Biol. 2009, 29:1060-1066.

Bruemmer et al., "Thiazolidinedione regulation of smooth muscle cell proliferation," The American Journal of Medicine, Dec. 8, 2003, 115(BA):87S-92S.

Dai et al., "LOX-1, a bridge between GLP-1 and mitochondrial ROS generation in human vascular smooth muscle cells," Biochemical and Biophysical Research Communications, 2013, 437:62-66.

Dios et al., "Troglitazone, but not rosiglitazone, inhibits na/h exchange activity and proliferation of macrovascular endothelial cells," Journal of Diabetes and its Complications, 2001, 15:120-127.

Dormandy et al., "Secondary prevention of macrovascular events in patients with type 2 diabetes in the PROactive Study (PROspective pioglitazone Clinical Trial in macrovascular events): a randomised controlled trial," Lancet, Oct. 8, 2005, 366:1279-89.

Dubey et al., "Pioglitazone attenuates hypertension and inhibits growth of renal arteriolar smooth muscle in rats," American Physiological Society, 1993, R726-R732.

Duckworth et al., "Glucose control and vascular complications in veterans with type 2 diabetes," The New England Journal of Medicine, Jan. 8, 2009, 360:129-139.

Ervinna et al., "Anagliptin, a dpp-4 inhibitor, suppresses proliferation of vascular smooth muscles and monocyte inflammatory reaction and attenuates atherosclerosis in male apo e-deficient mice," Endocrinology, Mar. 2013, 145(3):1260-1270.

Fukuda et al., "Troglitazone inhibits growth and improves insulin signaling by suppression of angiotensin ii action in vascular smooth muscle cells from spontaneously hypertensive rats," Atherosclerosis, 2002, 163:229-239.

Gaziano et al., "Effect of bromocriptine-qr (a quick-release formulation of bromocriptine mesylate) on major adverse cardiovascular events in type 2 diabetes subjects," J Am Heart Assoc, 2012, 1:doi:10.1161/JAHA.112.002279, 11 pages.

Gaziano et al., "Randomized clinical trial of quick-release bromocriptine among patients with type 2 diabetes on overall safety and cardiovascular outcomes," Diabetes Care, Jul. 2010, 33:1503-1508 (12 total pages).

Gerstein et al., "Effects of intensive glucose lowering in type 2 diabetes," The New England Journal of Medicine, Jun. 12, 2008, 358:2545-59.

Gerstein, "Basal insulin and cardiovascular and other outcomes in dysglycemia," The New England Journal of Medicine, Jul. 26, 2012, 367:319-328.

Goto et al., "Exendin-4, a glucagon-like peptide-1 receptor agonist, reduces intimal thickening after vascular injury, " Biochemical and Biophysical Research Communications, 2011, 405:79-84.

Gouni-Berthold et al., "Troglitazone and rosiglitazone inhibit the low density lipoprotein-induced vascular smooth muscle cell growth," Exp Clin Endocrinol Diabetes, 2001, 109:203-209.

Ha et al., "High glucose induces connective tissue growth factor expression and extracellular matrix accumulation in rat aorta vascular smooth muscle cells via extracellular signal-regulated kinase 1 / 2," Korean J Physiol Pharmacol, Aug. 2013, 17:307-314.

Hara et al., "Central dopaminergic function in stroke prone spontaneously hypertensive rats effects of chronic treatment with lisuride on the impaired swimming ability," Database Accession No. PREV198376013141 and Folia Pharmacologica Japonica, 1982, 80(5):395-394 (Abstract only—2 pages).

Hasko et al., "Modulation of lipopolysaccharide-induced tumor necrosis factor-α and nitric oxide production by dopamine receptor agonists and antagonists in mice," Immunology Letters, 1996, 49(3):143-147.

(56) References Cited

OTHER PUBLICATIONS

Home et al., "Rosiglitazone evaluated for cardiovascular outcomes in oral agent combination therapy for type 2 diabetes (record): a multicentre, randomised, open-label trial," Lancet, Jun. 20, 2009, 373:2125-35.
Hsueh et al., "Insulin signaling in the arterial wall," Am J Cardiol, 1999, 84:21J-24J.
Kuo et al., "Hypothalamic neuropeptide Y (NPY) and the attenuation of hyperphagia in streptozotocin diabetic rats treated with dopamine D1/D2 agonists," British Journal of Pharmacology, 2006, 148:640-647.
Lan et al., "Vascular fibrosis in atherosclerosis," Cardiovascular Pathology, 2013, 22:4101-407.
Lightell et al., "Loss of canonical insulin signaling accelerates vascular smooth muscle cell proliferation and migration through changes in p27kip1 regulation," Endocrinology, Feb. 2011, 152(2):651-658.
Lusis, "Atherosclerosis," Nature, 407(6801): 233-241, Sep. 14, 2000.
NCBI Reference Sequence XP-002587257, Hypothetical Protein BRAFLDRAFT-61678 (Branchiostoma floridae), Accession No. XP_002587257, GI No. 260784404, dated Oct. 8, 2009, (retrieved from the Internet: Feb. 23, 2015), 2 pages.
O'Neill et al., "Dopamine D2 receptor agonists protect against ischaemia induced hippocampal neurodegeneration in global cerebral ischaemia," European Journal of Pharmacology, Jul. 3, 1998, 352(1):37-46.
Park et al., "The inhibition of insulin-stimulated proliferation of vascular smooth muscle cells by rosiglitazone is mediated by the akt-mtor-p70s6k pathway," Yonsei Med J, 2008, 49(4):592-600.
Patel et al., "Intensive blood glucose control and vascular outcomes in patients with type 2 diabetes," The New England Journal of Medicine, Jun. 6, 2008, 358:2560-72.
Ratner et al., "Cardiovascular safety of exenatide BID: an integrated analysis from controlled clinical trials in participants with type 2 diabetes," Cardiovascular Diabetology, 2011, 10:22, 10 pages.
Schaper et al., "Peripheral vascular disease and Type 2 diabetes mellitus," Diabetes Metab Res Rev, 2000, 16(Suppl 1) S11-S15.
Schobel et al., "Effects of bromocriptine on cardiovascular regulation in healthy humans," Hypertension, 25(5):1075-1082, May 1995.
Scirica et al., "Saxagliptin and cardiovascular outcomes in patients with type 2 diabetes mellitus," The New England Journal of Medicine, Oct. 3, 2013, 369(14):1317-1326.
Stout, "Insulin as a mitogenic factor: role in the pathogenesis of cardiovascular disease," The American Journal of Medicine, Feb. 21, 1991, 90 (suppl 2A—62S-65S).
Takasawa, "Inhibition of dipeptidyl peptidase 4 regulates microvascular endothelial growth induced by inflammatory cytokines," Biochemical and Biophysical Research Communications, 2010, 401:7-12.
Turner, "Intensive blood-glucose control with sulphonylureas or insulin compared with conventional treatment and risk of complications in patients with type 2 diabetes (UKPDS 33)," UK Prospective Diabetes Study D (UKPDS) Group, The Lancet, Sep. 12, 1998, 352:837-853.
White et al., "Alogliptin after acute coronary syndrome in patients with type 2 diabetes," The New England Journal of Medicine, Oct. 3, 2013, 369(14):1327-1335.
Zou et al., "Protein-protein coupling/uncoupling enables dopamine d2 receptor regulation of AMPA receptor-mediated excitotoxicity," The Journal of Neuroscience, Apr. 27, 2005, 25(17):4385-4395.
First Office Action issued in CN Application No. 200880025452.8, dated Apr. 19, 2012, 11 pages (with English translation).
Second Office Action issued in CN Application No. 200880025452.8, dated Mar. 28, 2013, 15 pages (with English translation).
Third Office Action issued in CN Application No. 200880025452.8, dated Feb. 10, 2014, 8 pages (with English translation).
Fourth Office Action issued in CN Application No. 200880025452.8, dated Jan. 22, 2015, 14 pages (with English translation).
Office Action in CN Application No. 201180035790.1, dated Nov. 20, 2013, 20 pages.
Extended European Search Report issued in EP Application No. 08742225.9, dated Oct. 15, 2010, 12 pages.
Communication Pursuant to Article 94(3) EPC issued in EP Application No. 08742225.9, dated Dec. 23, 2014, 4 pages.
Extended European Search Report issued in EP Application No. 08768002.1, dated Jul. 8, 2010, 7 pages.
Communication Pursuant to Article 94(3) EPC issued in EP Application No. 08768002.1, dated Apr. 20, 2011, 4 pages.
Communication Pursuant to Article 94(3) EPC issued in EP Application No. 08768002.1, dated Jan. 15, 2014, 7 pages.
Opposition filed by Indian Pharmaceutical Alliance against corresponding Indian Patent Application No. 7696/DELNP/2009 (owned by VeroScience, LLC), Jan. 3, 2011, 38 pages.
First Examination Report issued in IN Application No. 7696/DELNP/2009, dated Jan. 7, 2015, 2 pages.
Office Action issued in JP Application No. 2010-510366, dated Oct. 4, 2013, 5 pages (with English translation).
Office Action issued in JP Application No. 2014-018636, dated Mar. 10, 2015, 8 pages (with English translation).
Office Action issued in MX Application No. MX/a/2009/012919, dated Sep. 19, 2011, 3 pages (with English translation).
Office Action issued in MX Application No. MX/a/2009/012919, dated Jun. 5, 2012, 6 pages (with English translation).
Office Action issued in MX Application No. MX/a/2009/012919, dated Feb. 11, 2013, 7 pages (with English translation).
Office Action issued in MX Application No. MX/a/2009/012919, dated Sep. 3, 2013, 7 pages (with English translation).
Non-final Office Action issued in U.S. Appl. No. 12/077,552, dated Jul. 7, 2011, 10 pages.
Final Office Action issued in U.S. Appl. No. 12/077,552, dated Apr. 10, 2012, 12 pages.
Final Office Action issued in U.S. Appl. No. 12/077,552, dated Jul. 16, 2013, 13 pages.
Non-final Office Action issued in U.S. Appl. No. 12/077,552, dated Feb. 10, 2014, 10 pages.
Final Office Action issued in U.S. Appl. No. 12/077,552, dated Oct. 22, 2014, 22 pages.
Non-final Office Action issued in U.S. Appl. No. 12/077,552, dated Sep. 15, 2015, 31 pages.
International Search Report and Written Opinion issued in International Application No. PCT/US2008/003849, dated Jun. 20, 2008, 7 pages.
International Preliminary Report on Patentability issued in International Application No. PCT/US2008/003849, dated Oct. 6, 2009, 7 pages.
International Search Report and Written Opinion issued in International Application No. PCT/US2008/006899, dated Aug. 29, 2008, 7 pages.
International Preliminary Report on Patentability issued in International Application No. PCT/US2008/006899, dated Dec. 1, 2009, 7 pages.
European Office Action in Application No. 07780943.0, dated May 10, 2017, 8 pages.
Mendels and Schless, "Comparative efficacy of alprazolam, imipramine, and placebo administered once a day in treatment depressed patients," Journal of Clinical Psychiatry, Jan. 1986, 47: 357-361.
Pijil et al., "Bromocriptine: A novel approach to the treatment of type 2 diabetes," Diabetes Care, Jan. 2000, 8: 1154-1161.
Wells et al., "Bromocriptine in treatment of depression," DICP, The Annals of Pharmacotherapy, Jul./Aug. 1989, 23: 600-602.

METHOD OF TREATING METABOLIC DISORDERS AND DEPRESSION WITH DOPAMINE RECEPTOR AGONISTS

This application claims the benefit of U.S. Provisional Patent Application No. 60/945,555, filed Jun. 21, 2007, which is hereby incorporated by reference in its entirety.

FIELD OF THE INVENTION

This invention relates to methods for simultaneously treating metabolic disorders and depression with dopamine receptor agonists.

BACKGROUND OF THE INVENTION

Dopamine agonists have been useful in the treatment of various diseases such as migraine headache, Parkinson's disease, acromegaly, hyperprolactinemia, prolactinoma, galactorrhea, amenorrhea, and metabolic disorders, including diabetes.

Diabetes, one of the most insidious of the major diseases, can strike suddenly or lie undiagnosed for years while attacking the blood vessels and nerves. Diabetics, as a group, are far more often afflicted with blindness, heart disease, stroke, kidney disease, hearing loss, gangrene and impotence. One third of all visits to physicians in the U.S. are occasioned by this disease and its complications, and diabetes and its complications are a leading cause of death in the U.S. and other countries.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. The ingested glucose is normally metabolized in the liver to $CO_2$ and $H_2O$ (50%); to glycogen (5%), and to fat (30-40%), which is stored in fat depots. Fatty acids are circulated, returned to the liver and metabolized to ketone bodies for utilization by the tissues. The fatty acids are also metabolized by other organs, fat formation being a major pathway for carbohydrate utilization. The net effect of insulin is to promote the storage and use of carbohydrates, protein and fat. Insulin deficiency is a common and serious pathologic condition in humans. In Type 1 diabetes the pancreas produces little or no insulin, and insulin must be injected daily for the survival of the diabetic. In Type 2 diabetes the pancreas produces insulin, but the amount of insulin is insufficient, or less than fully effective due to cellular resistance, or both, in either form there are widespread abnormalities, but the fundamental defects to which the abnormalities can be traced are (1) a reduced entry of glucose into various "peripheral" tissues and (2) an increased liberation of glucose into the circulation from the liver (increased hepatic glucogenesis). There is therefore an extracellular glucose excess and an intracellular glucose deficiency which has been called "starvation in the midst of plenty." There is also a decrease in the entry of amino acids into muscle and an increase in lipolysis. Thus, these result, as a consequence of the diabetic condition, in elevated levels of glucose in the blood, and prolonged high blood sugar, which is indicative of a condition which will cause blood vessel and nerve damage. Obesity, or excess fat deposits, is often associated with increasing cellular resistance to insulin, which precedes the onset of frank diabetes. Prior to the onset of diabetes, the pancreas of the obese are taxed to produce additional insulin; but eventually, perhaps over several years prior to the onset of frank type 2 diabetes, insulin productivity falls and diabetes results.

Obesity and insulin resistance, the latter of which is generally accompanied by hyperinsulinemia or hyperglycemia, or both, are hallmarks of Type 2 diabetes. Controlled diet and exercise can produce modest results in the reduction of body fat deposits. Hyperinsulinemia is a higher-than-normal level of insulin in the blood. Insulin resistance can be defined as a state in which a normal amount of insulin produces a subnormal biologic response. In insulin-treated patients with diabetes, insulin resistance is considered to be present whenever the therapeutic dose of insulin exceeds the secretory rate of insulin in normal persons. Insulin resistance is also found in the setting defined by higher-than-normal levels of insulin—i.e., hyperinsulinemia—when there are present normal or elevated levels of blood glucose.

Insulin is a hormone with a multitude of biological activities, many of which are tissue-specific. For example, insulin can augment milk production in the mammary gland, stimulate fat synthesis in the liver, promote the transport of glucose into muscle tissue, stimulate growth of connective tissues, and the like. The effects of the insulin molecule in one tissue are not necessarily dependent upon its effect in other tissues. That is, these insulin activities can be and air molecularly separate from each other. Dopamine receptor agonists (e.g., bromocriptine) are known to inhibit liver cell lipogenic (or fat synthesizing) responsiveness to insulin. But, appropriately timed daily administration of a dopamine agonist (e.g., bromocriptine) can be used to stimulate whole body (primarily muscle) tissue hypoglycemic (or glucose disposal) responsiveness to insulin, as described in U.S. Pat. No. 5,468,755, incorporated herein by reference in its entirety.

Many of the hormones involved in metabolic disorders, including diabetes, exhibit a daily rhythm of fluctuating serum levels. Such hormones include adrenal steroids, e.g., the glucocorticosteroids, notably cortisol, and prolactin, a hormone secreted by the pituitary gland. These daily rhythms provide useful indices for understanding and treating metabolic diseases. For example, peak concentration of prolactin occurs at different times of day in lean and fat animals.

The normal daily prolactin level profile of a healthy human is highly regular and reproducible, characterized by a low and relatively constant day level followed by a sharp night-time peak, returning to a low level by daytime. See U.S. Pat. No. 5,679,685, the contents of which are incorporated herein by reference. Altering the prolactin profile of a subject having a metabolic disorder or key element thereof to resemble that of a healthy subject of the same species and sex can provide therapeutic benefit to the subject. The circadian rhythm of plasma prolactin level "feedback" centrally to reset circadian dopaminergic activities that are critical in regulating peripheral glucose, lipid, and protein metabolism. Phase shifts in the circadian rhythm of dopamine release at the biological clock (the suprachiasmatic nuclei), from that observed in obese, insulin resistant animals to that observed in lean, insulin sensitive animals produces the lean insulin sensitive state. Dopamine agonists are useful agents for treatment of metabolic disease and/or key elements of metabolic disease and can be used to reset daily prolactin profiles in subjects with metabolic disease and/or exhibiting key elements thereof to that of healthy humans.

Previous studies have demonstrated that dopamine receptor agonists when administered at a predetermined time of day, generally in the morning in humans, can improve metabolic disorders including obesity, insulin resistance, glucose intolerance, impaired fasting glucose, metabolic syndrome, and Type 2 diabetes. It is also generally well-accepted that dopamine is a mood enhancer. It is well-established that approximately 30% of Type 2 diabetics have some form of clinical depression. Also, depression can be very common among obese patients and post-myocardial infarction patients. Moreover, anti-depressant medication use appears to be associated with diabetes risk (Diabetes Care, 31:420, 2008). The relationship between metabolic disorders such as Type 2 diabetes and depression, whether cause-effect or associational, has been the focus of much research and debate. It is clear that the coexistence of these disorders hampers the effective treatment of either disorder and therefore adversely influences the quality of life of these type patients. But, co-treatment of metabolic disorders and depression can be difficult insofar as most serotonin-enhancing anti-depressants and tricyclic anti-depressants that increase prolactin release potentiate or exacerbate metabolic disorders such as obesity, insulin resistance, and Type 2 diabetes.

There is a need in the art for methods of treating both metabolic disorders (including Type 2 diabetes) and depression. Accordingly, the methods of disclosed herein avoid problems associated with prior art approaches and improve the treatment of metabolic disorders and depression in patients suffering from both types of conditions. The methods disclosed herein avoid or reduce problems such as, e.g., the adverse effects of serotonin-enhancing anti-depressants on metabolic disorders, by treatment or co-treatment with one or more dopamine agonists. This co-treatment with one or more dopamine receptor agonists further allow for the reduction in dose of serotonin-enhancing anti-depressants and thereby reduce their negative impact on metabolism and metabolic disorders.

SUMMARY OF THE INVENTION

In certain embodiments, the invention provides a method for treating a metabolic disorder and depression comprising administering to a patient in need thereof a therapeutically effective amount of one or more dopamine receptor agonists.

In certain embodiments, the invention provides a method of treating a metabolic disorder and depression comprising administering to a patient in need thereof a therapeutically effective combination of a dopamine receptor agonist and an anti-depressant. Preferably, the dopamine receptor agonist is administered at a first predetermined time of day, e.g., in the morning, and the anti-depressant is administered at a second predetermined time of day, e.g., in the evening.

In certain embodiments, the metabolic disorder to be treated is Type 2 diabetes, obesity or cardiovascular disease.

In another embodiment, the dopamine receptor agonist is bromocriptine.

In another embodiment, the invention provides a dosage form comprising a first active agent and a second active agent, wherein said first active agent is an anti-depressant, said second active agent is a dopamine agonist, said first active agent is substantially released within 2 hours following administration of said dosage form and said second active agent is released substantially within the period within 2 hours of waking when said dosage is administered at bedtime.

DETAILED DESCRIPTION OF THE INVENTION

Disclosed herein are methods for treating one or more metabolic disorders (such as Type 2 diabetes) and depression, comprising administering to a patient in need thereof a therapeutically effective amount of a dopamine agonist and an anti-depressant.

Dopamine receptor agonists, when administered at the appropriate time of day, have the ability to improve both metabolic disorders, such as Type 2 diabetes, and depression. Moreover, in some cases, antidepressant medications may be reduced when used at the appropriate time of day in conjunction with dopamine receptor agonists and resultantly improve metabolic status, inasmuch as most serotonin-enhancing anti-depressants and prolactin-enhancing anti-depressants such as the tricyclics potentiate or exacerbate metabolic disorders such as obesity, insulin resistance, and Type 2 diabetes. That is, abnormal elevations in daytime (diurnal: 0500-2200) levels (versus nighttime levels) of central neuronal synaptic serotonin (e.g., SSRIs) or postsynaptic serotonergic activity or of plasma prolactin via pharmaceutical therapy may potentiate both the depressed state and metabolic disease, in fact the disorders such current standard treatment is aimed at ameliorating. The approach of the present invention is contrary to this approach and its results are contrary to the results of this approach. Serotonin-enhancing antidepressant agonists include agents that increase synaptic levels of serotonin (e.g., serotonin itself, serotonin precursors such as 5-hydroxy tryptophan or tryptophan, and selective serotonin reuptake inhibitors [SSRIs] and/or agents that increase post-synaptic serotonin function (e.g., post-synaptic serotonin receptor agonists). Furthermore, appropriately timed daily administration of dopamine receptor agonists and serotonin-enhancing anti-depressants may further improve (i.e., maximize) the interactive effectiveness of both to improve metabolic disease, such as Type 2 diabetes and depression. Generally, to achieve such a result, the dopamine receptor agonist would be given in the morning upon waking and the serotonin-enhancing anti-depressant would be given later in the day, possibly preferably in the evening before bedtime. In addition, administration of dopamine receptor agonists to treat depression in individuals with Type 2 Diabetes avoids side effects associated with the administration of anti-depressant dopamine/norepinephrine re-uptake inhibitors (dopamine re-uptake inhibitors that also inhibit re-uptake of norepinephrine from presynaptic neurons), via their influence to raise levels of synaptic norepinephrine, which could have negative metabolic health consequences in individuals with metabolic disorders such as obesity, cardiovascular disease and type 2 diabetes. The present invention avoids the complication and metabolic damage of increasing neuronal synaptic norepinephrine level while effectively treating metabolic disorders and depression and in many cases the present invention may reduce abnormally elevated neuronal synaptic norepinephrine level towards normal levels observed in healthy subjects. Elevated hypothalamic neuronal synaptic norepinephrine levels are believed to contribute to metabolic disease and therefore avoiding such an increase, as with dopamine receptor agonist therapy, is a benefit over those therapies that do increase synaptic norepinephrine levels.

The present invention provides methods of improving metabolic disorders and depression in subjects in need of such treatment by increasing abnormally low daytime dopaminergic neuronal activity (e.g., with dopamine receptor agonist therapy) and inhibiting or avoiding increases in daytime plasma prolactin and central synaptic serotonin levels and increasing nighttime central serotonin levels or neuronal activity and/or plasma prolactin levels. This method is not employed by any existing standard therapies for the treatment of metabolic disorders and depression.

Examples of dopamine receptor agonists may be non-ergot or ergot-related derivatives. These include $D_1$ dopamine receptor agonists and/or $D_2$ dopamine receptor agonists.

The methods disclosed herein may comprise administration of one or more $D_1$ dopamine receptor agonists and/or $D_2$ dopamine receptor agonists.

Therapeutically effective amounts of dopamine receptor agonist for humans and other vertebrates vary according to several factors, including patient characteristics and route of administration. For example, therapeutically effective amounts of $D_2$ agonist for humans and vertebrates when administered parenterally alone (not conjoined to a $D_1$ agonist) are typically within the range of about 0.5 μg/kg/day to about 300 μg/kg/day. Preferably, the therapeutically effective amounts of $D_2$ agonist for humans and vertebrates when administered alone are typically within the range of about 0.5 μg/kg/day to about 250 μg/kg/day. More preferably, the therapeutically effective amounts of $D_2$ agonist for humans and vertebrates when administered alone are typically within the range of about 0.5 μg/kg/day to about 200 μg/kg/day. Most preferably, the therapeutically effective amounts of $D_2$ agonist for humans and vertebrates when administered alone are typically within the range of about 1.0 μg/kg/day to about 150 μg/kg/day. Therapeutically effective amounts of $D_1$ agonist for humans and vertebrates when administered parenterally alone (not conjoined to a $D_2$ agonist) are typically within the range of about 1.0 μg/kg/day to about 10.0 mg/kg/day. Preferably, the therapeutically effective amounts of $D_1$ agonist for humans and vertebrates when administered alone are typically within the range of about 1.0 μg/kg/day to about 10.0 mg/kg/day. More preferably, the therapeutically effective amounts of $D_1$ agonist for humans and vertebrates when administer alone are typically within the range of about 1.0 μg/kg/day to about 7.0 mg/kg/day. Most preferably, the therapeutically effective amounts of $D_1$ agonist for humans and vertebrates when administered alone are typically within the range of about 2.0 μg/kg/day to about 5.0 mg/kg/day.

Where therapeutically effective amounts of $D_1$ and $D_2$ agonist(s) for humans and vertebrates are administered parenterally in conjunction, typically about 15% less of each of the $D_1$ and $D_2$ agonist(s) are used. Preferably, where therapeutically effective amounts of $D_1$ and $D_2$ agonist(s) for humans and vertebrates are administered parenterally in conjunction about 17% less of each of the $D_1$ and $D_2$ agonist(s) are used. More preferably, where therapeutically effective amounts of $D_1$ and $D_2$ agonist(s) for humans and vertebrates are administered parenterally in conjunction about 20% less of each of the $D_1$ and $D_2$ agonist(s) are used. Most preferably where therapeutically effective amounts of $D_1$ and $D_2$ agonist(s) for humans and vertebrates are administered parenterally in conjunction about at least 25% less of each of the $D_1$ and $D_2$ agonist(s) are used.

$D_1$ dopamine agonists activate or potentiate $D_1$ dopamine receptors. Examples of $D_1$ agonists include, without limitation, dopamine, apomorphine, SKF38393, dihydrexidine, SKF 75670, SKF 82957, SKF 81297, SKF 82958, SKF 82598, A77636, A68930, and SKF 82526 (fenoldopam), and racemic trans-10,11-dihydroxy 5,6,6a,7,8,12b-hexahydro and related benzazepine analogs, and those $D_1$ agonists disclosed in the references cited herein. A preferred $D_1$ dopamine agonist is SKF 38393 or apomorphine. See e.g., U.S. Pat. No. 6,855,707, the contents of which are incorporated herein in their entirety by reference.

$D_2$ dopamine agonists activate or potentiate $D_2$ dopamine receptors (e.g., $D_2$, $D_2$ short and $D_2$ long receptors, $D_4$, and $D_4$ dopamine receptors). In one embodiment, the $D_2$ agonist is a selective agonist for the $D_2$ receptor over the DL receptor. In a further embodiment, the $D_2$ agonist is a weak $D_1$ agonist or is not a $D_1$ agonist.

Ergot-related $D_2$ agonists include, for example and without limitation, 2-bromo-α-ergocriptine (bromcriptine), terguride, hydergine, 6-methyl 8β-carbobenzyloxy-aminoethyl-10-α-ergoline, 8-acylaminoergoline, 6-methyl-8-α-(N-acyl)amino-9-ergoline, lisuride, dihydro-alpha-ergocriptine, dihydro-alpha-ergotoxine, 6-methyl-8-α-(N-phenyl-acety)amino-9-ergoline, ergocornine, 9,10-dihydroergocornine, any D-2-halo-6-alkyl-8-substituted ergoline, and D-2-bromo-6-methyl-8-cyanomethylergoline. Of these bromocriptine, terguride, lisuride, dihydroergotoxine (hydergine) or ergot-related compounds with little or no serotonin $5HT_{2B}$ receptor agonist activity is most preferred.

Non-ergot-related dopamine $D_2$ agonists are selected from, for example and without limitation, ropinirole, piribedil, talipexole, quinelorane, and apomorphine.

A prolactin inhibitor (such as bromocriptine) can be administered to a mammalian subject (particularly to a human) at a predetermined time during a 24-hour period if that subject has abnormally high daytime prolactin levels (higher than any of the normal daytime levels for a subject of the same species and sex). The administration and its timing are designed to decrease the subject's abnormally high daytime prolactin levels. However, a prolactin stimulator may need to be administered at a different predetermined time during a 24-hour period, if the subject has abnormally low night-time prolactin levels, to increase these night-time prolactin levels to be preferably no lower than the normal night-time prolactin levels for the same sex. It is also possible that both a prolactin inhibitor and a prolactin stimulator may need to be administered at different times to the same subject to bring about both a decrease in daytime prolactin levels and an increase in night-time prolactin levels. Aberrations in the circadian rhythm of plasma prolactin (and potentially glucocorticosteroid hormone as well) may be a marker of depression as well as of metabolic disease and "resetting" the plasma prolactin rhythm with dopamine agonist administration in the morning and serotonin enhancing antidepressant agonists administration in the evening may provide additional therapeutic benefit to the metabolic disorder(s) and the depressed state.

The term "parenteral administration" is defined herein to mean a method of administration that provides for the absorption of a substantial amount of the drug through other than the gastric and/or intestinal mucosa of the GI tract.

Routes of parenteral administration include, without limitation, buccal, sublingual, subcutaneous, nasal, oral, otic, ocular, rectal, vaginal, or upper respiratory mucosa, or through the skin or lungs. Accordingly, the dosage forms include, without limitation, injection, oral, otic, ophthalmic, or nasal sprays or drops, sublingual and/or buccal sprays, drops, tablets, solutions, colloidal suspensions, and/or ointments, hard capsule and soft capsules, tablets, coated tablets, or sachets, lozenge, films, chewing gum, chewable tablet, liquid gargle, skin patch, ointment, lotion, or cream, a respiratory inhaler, aerosols, or rectal or vaginal suppository. Injection can be, for example, subcutaneous, intradermal, and/or intraperitoneal. Methods of nasal administration include nasal sprays and/or drops and/or application of nasal ointments. Methods of sublingual or buccal administration include oral spays, drops, solutions, colloidal suspensions, tablets, ointments, lozenges, films, chewing gums, chewable tablets, and/or liquid gargle. Methods of auricular or ocular administration include sprays, drops, ointments, lotions and/ or creams. Methods of rectal administration include suppository, spray, drops, ointment, lotion and/or cream. Methods of vaginal administration include suppository, spray, drops, ointment, lotion and/or cream. Methods of upper respiratory mucosa or pulmonary administration include a respiratory inhaler, e.g., nebulizer. Methods of transdermal administration include skin patches, dermal spray, drops, ointment, lotion, gel and/or cream.

Preferred routes of administration for dopamine receptor agonists are subcutaneous injection, buccal, sublingual, nasal and transdermal. More preferred routes of administration are buccal, sublingual and nasal. Particularly preferred routes of administration include subcutaneous injections, sublingual or buccal dosage forms, and transdermal application for example via skin patches.

Where parenteral administration is accomplished via oral administration, absorption through the gastric and/or intestinal mucosa can be substantially prevented by the use of certain components in the formulation such as bioadhesives, permeabilizing agents and stabilizers that prevent and/or reduce the introduction of dopamine agonists into the gastric and/or intestinal mucosa of the GI tract.

The term "metabolic disorder" includes disorders associated with aberrant whole-body glucose, lipid and/or protein metabolism of a species and pathological consequences arising there from. These metabolic disorders may or may not be associated with aberrant patterns in the daily levels (and fluctuations) of prolactin secretion.

The "key elements" of these metabolic disorders include but are not limited to, Type 2 diabetes, prediabetes (impaired fasting glucose or impaired glucose tolerance), metabolic syndrome or indices (key elements) thereof (increased waist circumference, increased fasting plasma glucose, increased fasting plasma triglycerides, decreased fasting high density lipoprotein level, increased blood pressure), insulin resistance, hyperinsulinemia, cardiovascular disease (or key elements thereof such as arteriosclerosis, coronary artery disease, peripheral vascular disease, or cerebrovascular disease), congestive heart failure, obesity, elevated plasma norepinephrine, elevated cardiovascular-related inflammatory factors, elevated plasma factors potentiating vascular endothelial dysfunction, hyperlipoproteinemia, arteriosclerosis or atherosclerosis, hyperphagia, hyperglycemia, hyperlipidemia, and hypertension or high blood pressure, increased plasma postprandial triglyceride or free fatty acid levels, increased cellular oxidative stress or plasma indicators thereof, increased circulating hypercoagulative state, renal disease including renal failure and renal insufficiency.

As used herein, the term "pharmaceutically acceptable" refers to a biologically or pharmacologically compatible drug component for in vivo use, and preferably means a drug component approved by a regulatory agency of the Federal or a state government or listed in the U.S. Pharmacopoeia or other generally recognized pharmacopoeia for use in animals, and more particularly in humans.

The term "bioavailability" refers to the rate and extent to which a dopamine agonist is absorbed into a biological system from an administered drug product and becomes available at the site of biological action.

As used herein, a "therapeutically effective amount" refers to the amount of an active agent, such as a dopamine receptor agonist or an antidepressant, sufficient to treat the targeted disease in the patient.

Prolactin Cycle & Dopamine Agonists

Healthy (normal) subjects, i.e., lean members of a species not suffering from such metabolic disease and/or key elements thereof have highly predictable daily prolactin release profiles. In humans these release profiles are characterized by a low and relatively constant prolactin level during the waking hours (day) followed by a sharp rise to a peak during sleep (night) and subsequent more gradual tapering down to the waking hours level by morning. One or more dopamine receptor agonist can be administered to a subject in need thereof to modify aberrant daily prolactin level rhythms so that they resemble, or more closely approximate in phase and amplitude, the normal diurnal plasma prolactin level rhythms of lean, young and healthy members of the same species and sex. See e.g., U.S. Pat. Nos. 5,468,755; 5,496,803; 5,344,832, 5,585,347, 5,830,895, and 6,855,707 and PCT applications US93/12701 and US95/09061 (the disclosure of which is incorporated herein by reference). Such modulation of prolactin rhythms has been used to treat Type 2 diabetes, obesity, insulin resistance, and hyperinsulinemia or hyperglycemia, hyperlipoproteinemia, hyperphagia, obesity, insulin resistance (impaired glucose tolerance), hyperlipidemia, etc.

A relationship exists between obesity and insulin resistance, and that obesity can lead to increased insulin resistance. Likewise, the circadian rhythms of plasma prolactin and glucocorticosteroid concentrations, respectively, have important consequences in the regulation of body fat stores, and that the phase relationship between the prolactin and glucocorticosteroid levels, respectively, differ in lean and fat animals. In a fat animal, prolactin will reach a peak level at a given hour of a 24 hour period (in a human usually near midday), and the prolactin level of a lean animal at another time of day (in a human usually during sleep). In a lean animal the glucocorticosteroids, e.g., cortisol, will peak during a 24 hour period at a given hour (generally at a time different from that of prolactin; in a human generally within a few hours of waking. Thus, the phase relations of the cortisol and prolactin rhythms differ in lean and fat animals. The peak periods of prolactin and glucocorticosteroid production, respectively, may differ to some extent between male and females of any given species. This being so, daily dosages of a dopamine agonist, or prolactin inhibitor, given to an obese subject shortly after the normal time of day that the prolactin is at its peak in a lean subject of the same species and sex will produce a weight reduction in the obese subject. Such treatment will, if continued over a sufficient period, reset on a long term or permanent basis the phase of the neural oscillation for the prolactin rhythm, or the phases of the neural oscillations for both the prolactin and glucocorticosteroid rhythms in the obese individual to that present in a lean subject. The obese subject, on initiation of the treatment with the dopamine agonist, or prolactin inhibitor, will lose body fat stores, and the body fat deposits of the obese subject on continuation of the treatments on a daily basis will drop to and stabilize at that of a lean subject of the same species. On discontinuing the daily treatments, the rise and fall of the prolactin, or prolactin and glucocorticosteroid levels in the blood of the treated patient on a daily basis will correspond to that of a lean subject of the same species, and for a period of long duration. The effect of resetting the prolactin, or prolactin and glucocorticosteroid rhythms, in this manner also increases the sensitivity of the cells of the subject to insulin, reduces hyperinsulinemia or hyperglycemia, or both, and thus alters long term pathologies which are characteristic of the onset of Type 2 diabetes. This effect of resetting the prolactin or prolactin and glucocorticosteroid rhythm, via timed daily administration of dopamine receptor agonists and serotonin-enhancing agents may also improve the depressed state as well.

Administration of Dopamine Agonist(s)

The amount of the dopamine agonist(s) to be administered to a patient may vary, depending for example on the weight of the patient and the nature or severity of the metabolic disease or the key elements thereof. An effective amount of the dopamine agonist(s) may be administered in one or more dosage forms, either simultaneously or at different times, and a dopamine agonist may be administered either separately or in conjunction with other dopamine agonist(s).

Preferably, the dopamine receptor agonist(s) may be administered to a patient in need thereof in a single daily dose of about 0.01 to about 50.0 mg of active agent. The preferred range is 0.02 to 50 mg of active agent, the more preferred range is 0.02 to 25 mg of active agent and the most preferred range is 0.1 to 25 mg of active agent.

Conjoined administration of one or more dopamine $D_1$ agonist with one or more $D_2$ agonist results in synergistic effects in improvement of one or more metabolic indices related to glucose or lipid metabolism, and thus an improved modification or regulation of at least one of glucose and lipid metabolism.

The administration of the $D_2$ agonist is preferably timed. The $D_2$ agonist can be administered at a predetermined time.

The administration of the $D_1$ agonist is preferably timed. The $D_1$ agonist is administered at a predetermined time. Because the $D_1$ agonist amplifies the effect of the conjoined $D_2$ agonist, it is advantageous to administer the $D_1$ agonist at or about the time of administration of the conjoined $D_2$ agonist(s), such that the activity period of the $D_1$ agonist in the bloodstream of the treated subject overlaps (in fact preferably overlaps as much as possible) with the activity period of the conjoined $D_2$ agonist(s).

Preferably, the dopamine receptor agonist(s) are administered once daily. More preferably, the dopamine receptor agonist(s) are administered once daily in the morning. Most preferably, the dopamine receptor agonist(s) are administered once daily at a predetermined time for bioavailability in the morning at a point after the peak in plasma prolactin level.

Dopamine receptor agonist(s) are preferably administered in the morning from about 0400 to about 1200 hour. More preferably, the dopamine receptor agonist(s) are administered in the morning from about 0500 to about 1200 hour. Most preferably, the dopamine receptor agonist(s) are administered in the morning from about 0500 to about 1000 hour.

For treating vertebrates, dosages of dopamine agonists are typically administered over a period ranging from about 10 days to about 180 days, or longer (e.g., greater than or equal to 1 year). However, patients, e.g., patients in particularly poor physical condition, or those of advanced age, may require longer, or even continuous, treatment. A treatment duration exceeding six months or even continuous treatment may be desirable, even when not required.

Administration of $D_1$ and $D_2$ agonists typically lead to improvement of at least one condition or indices indicative of a metabolic disorder.

The methods of the present invention are particularly suited for treatment of metabolic disorders and/or key elements of these disorders including but not limited to, Type 2 diabetes, prediabetes (impaired fasting glucose or impaired glucose tolerance), metabolic syndrome or indices (key elements) thereof (increased waist circumference, increased fasting plasma glucose, increased fasting plasma triglycerides, decreased fasting high density lipoprotein level, increased blood pressure), insulin resistance, hyperinsulinemia, cardiovascular disease (or key elements thereof such as arteriosclerosis, coronary artery disease, peripheral vascular disease, or cerebrovascular disease), congestive heart failure, obesity, elevated plasma norepinephrine, elevated cardiovascular-related inflammatory factors, hyperlipoproteinemia, atherosclerosis, hyperphagia, hyperglycemia, hyperlipidemia, and hypertension or high blood pressure, increased plasma postprandial triglyceride or tree fatty acid levels, increased cellular oxidative stress or plasma indicators thereof, increased circulating hypercoagulative state, renal disease including renal insufficiency.

Combination Therapy with Dopamine Agonists and Anti-Depressants

In preferred embodiments, patients suffering from a metabolic disease and depression are treated with a combination of a dopamine agonist and an anti-depressant. It has been found surprisingly that combination treatment of such patients is unexpectedly enhanced when a dopamine agonist is administered at a pre-determined first time of day and an anti-depressant is administered at a different, pre-determined second time of day, compared to administering the dopamine agonist and the anti-depressant at the same time of day.

A preferred pre-determined time of day for administering a dopamine agonist, e.g., when used in combination with an anti-depressant, is in the morning, e.g., at 0400 to 1200 hours, preferably within 1-2 hours and, more preferably, within 30 minutes of waking. A preferred pre-determined time for administering an anti-depressant, e.g., when used in combination with a dopamine agonist, is at night, e.g., at 2000 to 2400 hours, preferably within 1-2 hours and, more preferably, within 30 minutes of bedtime.

In certain embodiments, a dopamine agonist is administered at a pre-determined first time of day and an anti-depressant is administered at a different, pre-determined second time of day, by administering a single dosage form that provides for the release of a dopamine agonist and an anti-depressant at different times following administration. Thus, following administration, a dosage form may first release the anti-depressant, followed several hours later by the release of the dopamine agonist. Such a dosage form is preferably is taken at bedtime to produce introduction to the circulation of the antidepressant at around bedtime (around 2200 to 2400 hours) and introduction to the circulation of the dopamine agonist within 0400 to 1200 hours will produce the desired beneficial effect on metabolic disorders and depression. Alternatively, following administration, a dosage form my first release the dopamine agonist, followed several hours later by the release of the anti-depressant. Such a dosage is preferably is taken in the morning, more preferably upon waking, e.g., at 0400 to 1200, hours to produce introduction to the circulation of the dopamine agonist and introduction of the anti-depressant several hours later, e.g., at around bedtime (around 2200 to 2400 hours).

Thus in certain embodiments, the invention provides a composition, e.g., a dosage form, comprising a first active agent and a second active agent, wherein said active agents are released at substantially different times following administration of the dosage form. In certain embodiments, the first and second active agents are substantially released, e.g., 1, 2, 3, 4, 5, 6, 7, 8, 9, 10, 11, 12, 13, 14, 15, 16, 17, 18, 19, or 20 hours apart following administration of the dosage form. In certain embodiments, the first and second active agents are substantially released 1-4, 1-6, 1-8, 1-10, 1-12, 1-14, 1-16, 1-18, 1-20, 2-4, 2-6, 2-8, 2-10, 2-12, 2-14, 2-16, 2-18, 2-20, 3-6, 3-8, 3-10, 3-12, 3-14, 3-16, 3-18, 3-20, 4-8, 4-10, 4-12, 4-14, 4-16, 4-18, 4-20, 6-10, 6-12, 6-14, 6-16, 6-18, 6-20, 8-10, 8-12, 8-14, 8-16, 8-18, 8-20, 10-12, 10-14, 10-16, 10-18, 10-20, 12-14, 12-16, 12-18, 12-20, 14-16, 14-18, 14-20, 16-18, 16-20 or 18-20 hours apart following administration of the dosage form. In certain embodiments, said first active agent is a dopamine agonist and second active agent is an anti-depressant. In certain embodiments, said first active agent is an anti-depressant and said second active agent is a dopamine agonist. In a preferred embodiment said first active agent is an anti-depressant, said second active agent is a dopamine agonist and said active agents are released 4-12 hours apart. In certain embodiments, said first active agent is a dopamine agonist and said second active agent is an anti-depressant. In certain embodiments said first active agent is a dopamine agonist, said second active agent is an anti-depressant and said active agents are released 12-16 hours apart. More preferably each of said aforementioned dosage forms provide for the first active agent to be released within 2 hours following administration of the dosage form. Also preferred are dosage forms wherein said first agent is an anti-depressant that is released within 2 hours following administration and said second active agent is a dopamine agonist that is released within 2 hours of waking, when said dosage form is administered at bedtime.

In certain embodiments, a dopamine agonist and an anti-depressant are administered in amounts that together constitute a therapeutically amount for treating a metabolic disorder and/or depression, but which would not separately constitute a therapeutic amount, i.e., either one or both of the amount(s) of dopamine agonist and anti-depressant is administered at a sub-threshold amount.

Administration of Anti-Depressants

Therapeutic administration of anti-depressants is well known in the art. Examples of anti-depressants and guidance on their use for treating depression is found, for example, in Baldessarini, R. J., (2006). Drug Therapy of Depression and Anxiety, Chapter 17 in Goodman & Gilman's, The Pharmacological Basis of Therapeutics, eleventh edition, Brunton, L. L., et al. (ed.), Magraw-Hill, New York, pages 429-459, the content of which is incorporated herein by reference in its entirety. Preferred anti-depressants for combination treatment with dopamine agonists are serotonin enhancing agents, e.g., SSRIs, serotonin, 5-hydroxytryptophan, and tryptophan, tricyclics, e.g., phenothiazines, tertiary amine tricyclics and secondary amine tricyclics, and atypical anti-depressants. Examples of SSRIs include, without limitation, fluoxetine and paroxetine. Examples of tertiary amine tricyclics include, without limitation, amitriptylen, doxepin, imipramine and trimipramine. Examples of secondary amine tricyclics include, without limitation, amoxapine, desipramine and nortiptyline. Examples of atypical anti-depressants (including atypical anti-psychotics, see Baldessarini et al., Pharmacotherapy of Psychosis and Mania, Chapter 18, pp. 461-500 in Goodman &. Gilman, supra, the content of which is incorporated herein by reference in its entirety) include, without limitation, duloxetine, and mirtazapine.

EXAMPLES

The following example represents certain embodiments of the invention. The example is illustrative only and is not intended to limit the invention.

Example 1: Effect of Once-Daily, Morning Administration of Dopamine D2 Receptor Agonist on Depression Adverse Event Reporting Rate, Adverse Cardiovascular Event Rate, and Hyperglycemia in Type 2 Diabetes Patients A large proportion of subjects with type 2 diabetes have cardiovascular disease (approximately 65% of subjects with type 2 diabetes die of cardiovascular disease related events) and approximately 30% have some form of depression. The impact of Cycloset (a quick-release formulation of bromocriptine mesylate) upon hyperglycemia, adverse cardiovascular event rate, and depression adverse event reporting rate was assessed in a broad population of subjects with type 2 diabetes, many of which having cardiovascular disease risk factors, and many diagnosed with depression at study entry.

A 52 week, double blind, 2:1 randomized, multicenter study was conducted in patients with type 2 diabetes receiving a diabetes therapeutic regimen consisting of diet or no more than two hypoglycemic agents or insulin with or without one additional oral agent that were randomized to treatment with Cycloset (titrated from 1.6 mg/day to a maximal tolerated dose up to 4.8 mg daily; n=2,054), or placebo (n=1,016) (The Cycloset Safety Trial). Subjects were instructed to take their study drug (Cycloset or placebo) once daily in the morning upon awakening. If the subject missed taking the study drug within two hours of awakening, the subject was instructed to skip that day's dose and resume dosing the next morning. Subjects taking serotonin-potentiating anti-depressants were instructed to take such medications in the evening unless contraindicated to do so by sound medical practice or drug labeling. Inclusion criteria included subjects aged 30-80 with Type 2 diabetes, an HbA1C of ≤10.0 and BMI≤43. All adverse events were recorded by investigational site personnel from hospital records, subject-derived information, or subject-associated health care individuals associated with the event, per the specified study protocol and subject Informed Consent Form and in compliance with ICH guidelines and Good Clinical Practice Standards.

The primary and secondary endpoints were time to first all-cause serious adverse event (SAE) and cardiovascular SAE (composite of myocardial infarction, stroke, coronary revascularization, hospitalization for angina and hospitalization for congestive heart failure), respectively, which were adjudicated by an independent review committee. A pre-specified analysis of the between-treatment differences in HbA1c following 24 weeks of therapy among a subpopulation of subjects receiving metformin and sulfonylurea and HbA1c of ≥7.5 at baseline was also perforated.

There were 176 Cycloset and 98 placebo subjects that experienced a SAE, yielding a rate ratio of 0.88 and a hazard ratio of all cause SAE of 1.023 (96% one sided confidence limit of 1.27). There were 31 (1.5%) cardiovascular SAEs in the Cycloset group and 30 (3.0%) events in the placebo group resulting in a 42% reduction in cardiovascular outcomes in Cycloset treated subjects versus placebo (HR=0.58, 95% CI: 0.35-0.96; P=0.036). The incidence rate ratio for each of the components of the cardiovascular composite was less than 1.0. Among the metformin and sulfonylurea treated subpopulation of subjects, Cycloset (n=121) treatment resulted in an HbA1c reduction of −0.674 from baseline versus an increase for placebo (n=71) of 0.015 to give a placebo-adjusted change from baseline of −0.69 (P<0.0002). Of these Cycloset treated subjects, 39% (vs. 11% placebo) reached the American Diabetes Association goal of HbA1c≤7.0 (P<0.0007) and 53% (vs. 21% placebo) experienced a minimum reduction in HbA1c from baseline of 0.7 (p<0.0001).

Cycloset significantly reduced the risk for the a priori adjudicated cardiovascular adverse event endpoint and was comparable to placebo for all other serious adverse events for the entire study population. Among individuals inadequately controlled on metformin and sulfonylurea, 24 weeks of Cycloset therapy significantly improved glycemic control relative to placebo.

Cycloset had a statistically significant benefit on the pre-specified CVD composite endpoint of myocardial infarction (MI), stroke, coronary revascularization, hospitalization for angina or congestive heart failure (42% risk reduction [RR]; p=0.036). Another analysis includes a post-hoc analysis from this Cycloset Safety Trial that assesses the effect of Cycloset on the time to first occurrence of major adverse cardiovascular events (MACE) defined as the composite of ML stroke and CVD death and additional planned analysis of the influence of Cycloset on the CVD composite endpoint stratified by the baseline median HbA1c. CVD risk estimates were estimated as a hazard ratio [HR] and 95% confidence interval [CI] on the basis of the Cox proportional-hazards regression. Cycloset had a statistically significant beneficial effect on the risk of myocardial infarction, stroke and CVD death (55% RR; p=0.049). Among subjects with HbA1c≤7.0 there were fewer CVD events on Cycloset (15, n=1219) compared to placebo (18, n=615). For those with HbA1c>7.0 CVD events were also less on Cycloset (16, n=830) compared to placebo (12, n=400). The HR of the CVD composite endpoint for subjects with a baseline HbA1c of ≤7.0 or >7.0 was 0.48 (95% CI 0.24-0.95) or 0.74 (95% CI 0.35-1.56), respectively. Additionally, the beneficial reduction in the CVD composite endpoint was apparent regardless of age, gender or race. Cycloset significantly reduced the risk for myocardial infarction, stroke, and cardiovascular death. The macrovascular risk reduction for the pre-specified cardiovascular composite endpoint was apparent even among subjects with good glycemic control.

The number of adverse events related to depression, adjustment disorder, depressed mood, and suicide attempt, and the number of serious adverse events related to depression, suicide, and suicide attempt are reported in Table 1, below.

TABLE 1

| Adverse Events Reported | Cycloset (2054 subjects) | Placebo (1016 subjects) |
|---|---|---|
| Depression | 13 | 12 |
| Adjustment disorder with depressed mood | 0 | 1 |
| Depressed mood | 2 | 1 |
| Suicide attempt | 0 | 2 |
| **Serious Adverse Events Reported** | **Cycloset** | **Placebo** |
| Depression | 2 | 0 |
| Suicide | 1 | 0 |
| Suicide attempt | 0 | 1 |
| **TOTALS** | **Cycloset** | **Placebo** |
| # of Adverse or Serious Adverse Events Reported | 18 | 17 |
| % of subjects reporting | 0.87 (18/2054) | 1.67 (17/1016) |

Type 2 diabetic subjects exposed to Cycloset experienced depression-related adverse events at a rate 48% less than when exposed to placebo.

The incidence of adverse event reporting for depression, depression-related symptoms, suicide, and suicide attempts was substantively reduced among Type 2 diabetes subjects treated with Cycloset versus placebo. Also, glycemic control was significantly improved in the Cycloset group versus the placebo control group, as evidenced in part by a relative reduction in HbA1c level.

The present invention is not to be limited in scope by the specific embodiments described herein. Indeed various modifications of the invention in addition to those described herein will be apparent to those skilled in the art from the foregoing description. Such modifications are intended to fall within the scope of the appended claims.

It is further to be understood that all values are approximate and are provided for description. All references cited and discussed in this specification are incorporated herein by reference in their entirety and to the same extent as if each reference was individually incorporated by reference.

What is claimed is:

1. The method of treating a patient afflicted with type 2 diabetes and depression that is taking a serotonin enhancing anti-depressant comprising administering to a patient in need of such treatment a therapeutically effective amount of one or more dopamine receptor agonists daily at a first pre-determined time of day in the morning.

2. The method of claim 1, wherein the pre-determined time of day is between 0400 and 1200 hoursin the morning.

3. The method of claim 2, wherein the pre-determined time of day is upon waking.

4. The method of claim 1, wherein the dopamine receptor agonist is at least one of a dopamine D1 receptor agonist or a dopamine D2 receptor agonist.

5. The method of claim 1, wherein the dopamine receptor agonist is an ergot-related compound.

6. The method of claim 1 wherein the dopamine receptor agonist is selected from the group consisting of lisuride, terguride, dihydroergotoxine (hydergine), and bromocriptine.

7. The method of claim 1 wherein the dopamine receptor agonist is bromocriptine.

8. The method of claim 4 wherein the dopamine receptor agonist is a dopamine D1 receptor agonist.

9. The method of claim 4 wherein the dopamine receptor agonist is a dopamine D2 receptor agonist.

10. The method of claim 8 wherein the therapeutically effective amount is between about 0.01 to about 50.0 mg/kg.

11. The method of claim 10 wherein the therapeutically effective amount is between about 0.1 to about 25.0 mg/kg.

12. The method of treating a patient afflicted with type-2 diabetes and depression that is taking a serotonin enhancing anti-depressant comprising administering to a patient in need of such treatment a therapeutically effective amount of a D1 dopamine receptor agonist and a D2 dopamine receptor agonist once daily at a predetermined time for bioavailability in the morning and at a point after the peak in plasma prolactin level.

13. A method of treating a patient suffering from pre-diabetes and depression that is taking a serotonin enhancing anti-depressant comprising administering to a patient in need of such treatment a therapeutically effective amount of one or more dopamine receptor agonists daily at a first pre-determined time of day in the morning.

14. The method of claim 13 wherein the pre-determined time of day is between 0400 and 1200 hours in the morning.

15. The method of claim 13 wherein the predetermined time of day is within 2 hours of waking.

* * * * *

UNITED STATES PATENT AND TRADEMARK OFFICE
CERTIFICATE OF CORRECTION

PATENT NO. : 9,925,186 B2
APPLICATION NO. : 14/814018
DATED : March 27, 2018
INVENTOR(S) : Anthony H. Cincotta It is certified that error appears in the above-identified patent and that said Letters Patent is hereby corrected as shown below:

On the Title Page

Page 2, Column 1 (Other Publications), Line 24, delete "Pip" and insert -- Pijl --, therefor.

In the Specification

Column 1, Line 51, delete "both, in" and insert -- both. In --, therefor.

Column 2, Line 25, delete "air" and insert -- are --, therefor.

Column 5, Line 34, delete "administer" and insert -- administered --, therefor.

Column 6, Line 2, delete "DL" and insert -- $D_1$ --, therefor.

Column 6, Line 6, delete "(bromcriptine)," and insert -- (bromocriptine), --, therefor.

Column 6, Line 11, delete "-acety)" and insert -- -acetyl) --, therefor.

Column 8, Line 34, delete "prolactin;" and insert -- prolactin); --, therefor.

Column 10, Line 7, delete "tree" and insert -- free --, therefor.

Column 11, Line 31 (approx.), delete "(2006)." and insert -- (2006), --, therefor.

Column 11, Line 34, delete "Magraw-" and insert -- Mcgraw- --, therefor.

Column 11, Lines 43-44, delete "amitriptylen," and insert -- amitriptyline, --, therefor.

Column 11, Line 46, delete "nortiptyline." and insert -- nortriptyline. --, therefor.

Signed and Sealed this
Twelfth Day of May, 2020

Andrei Iancu
*Director of the United States Patent and Trademark Office*

Column 12, Line 44, delete “perforated.” and insert -- performed. --, therefor.

Column 13, Line 12, delete “ML” and insert -- MI, --, therefor.

In the Claims

Column 14, Line 24, Claim 2, delete “hoursin” and insert -- hours in --, therefor.